United States Patent [19]

Blandamura

[11] 4,344,942
[45] Aug. 17, 1982

[54] PHARMACOLOGICAL USE OF CYPROTERONE ACETATE

[75] Inventor: Manlio Blandamura, Rome, Italy

[73] Assignee: Finchimica S.R.L., Milan, Italy

[21] Appl. No.: 279,545

[22] Filed: Jul. 1, 1981

[51] Int. Cl.³ .............................................. A61K 31/56
[52] U.S. Cl. .................................................. 424/243
[58] Field of Search ........................................ 424/243

[56] References Cited

U.S. PATENT DOCUMENTS 3,338,893 8/1967 Beard et al. ................... 260/397.45
3,937,700 2/1976 Van Kamp et al. ................ 424/243

Primary Examiner—Elbert L. Roberts
Attorney, Agent, or Firm—Oblon, Fisher, Spivak, McClelland & Maier

[57] ABSTRACT

The 6-chloro-1,2α-methylene-4,6-pregnadien-17α-ol-3,20-dione-17-acetate (Cyproterone acetate) is a well known compound provided with a remarkably high anti-androgen activity. It has now surprisingly been found that the Cyproterone acetate shows an equally high anti-estrogen activity in menopause or pre-menopause women and can be used for treating women having cystic glandular hyperplasia of the endometrium.

2 Claims, No Drawings

PHARMACOLOGICAL USE OF CYPROTERONE ACETATE

The present invention relates to a new pharmacological use, as anti-estrogen, of the 6-chloro-1,2α-methylene-4,6-pregnadiene-17α-ol-3,20-dione-17-acetate (Cyproterone acetate).

The compound has the following structural formula:

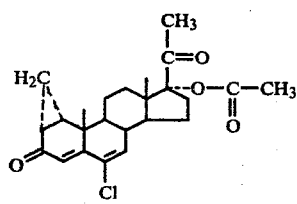

and has been first prepared and claimed by R. Wiechert, U.S. Pat. No. 3,334,093 (Feb. 8, 1966) to Schering Akt.

The compound has been till now used, in the pharmacological field, because its remarkable anti-androgen activity, as described by K. Iunkmann and F. Neumann, Acta endocrinol., suppl. 90, 139–154 (1964); F. Neumann et al., Endocrinology, 75, 428–33 (1964); F. Neumann et al., Acta endocrinol. 53, 382–90 (1966); M. Kramer et al., Naunyn-Schmiedelsbergs Arch. exp. Path Pharm. 251, 124–5(1965) and F. Neumann, Medizinische Klinik Wochenscr. fuer Klinik and Praxis, 68 Jahrgang, Heft 11, 329–333 (1973). As the Cyproterone acetate inhibits, by competition, the bounding of the androgen hormones to the cellular receptors of the target organs, it has exclusively been used, in the woman, as anti-androgen.

According to the present invention, it has surprisingly been found that the use of the Cyproterone acetate, following the RIA dosages, gives rise to a steady fall of the estrogen steroid hormones in the menopause and pre-menopause women. As reference, for the clear explanation of this new use of the Cyproterone acetate, of the involved dosages and of the resulting pharmacological effects, the following Table reports the treatment with Cyproterone acetate in seven cases of menopause or pre-menopause women suffering of cystic glandular hyperplasia of the endometrium (a pathologic state which, notoriously, is sustained by an iper-estrogen activity).

The treatment has been carried out by oral route, at a dosage of 200 to 400 mg daily (the dosage was related to the body area), the course of the treatment beeing of 30 days cycles for each. The results of the RIA dosages, before and after the treatment are reported in the Table.

Estrogen hormones— Estrogen hormones levels in the plasma (RIA) before and after the treatment with "Cyproterone acetate". 200 mg daily for cycles of 30 days each.

| | ENDOMETRIO | | | ESTRADIOL p.g./ml | | | ESTRIOL p.g./ml | | |
|---|---|---|---|---|---|---|---|---|---|
| | before treatment | After I cycle | After II cycle | Basal | After I cycle | After II cycle | Basal | After I cycle | After II cycle |
| N. 688 A. 1979 Age 57 | Cystis glandular hyperplasia | Secretory react. decid. stroma | Secretory react. decid. stroma | 180 | 14 | | 12 | trace | |
| N. 670 A. 1979 Age 50 | Cystis glandular hyperplasia | Secretory react. decid. stroma | Secretory react. decid. stroma | 151 | 10.5 | 16.2 | 16.9 | trace | 1.6 |
| N. 763 A. 1979 Age 49 | Cystis glandular hyperplasia | Secretory react. decid. stroma. | Secretory react. decid. stroma | 298 | 19 | | 23.3 | trace | |
| N. 788 A. 1979 Age 48 | Cystis glandular hyperplasia | Secretory react. decid. stroma | Secretory react. decid. stroma | 194 | 14.2 | 35 | 19 | 1.4 | 2.8 |
| N. 792 A. 1979 Age 44 | Cystis glandular hyperplasia | Secretory react. decid. stroma | Secretory react. decid. stroma | 84 | 10.2 | | 12.3 | trace | |
| N. 807 | Proliferative | Secretory | Secretory | 77 | 14 | | 7 | 1 | |

-continued

Estrogen hormones— Estrogen hormones levels in the plasma (RIA) before and after the treatment with "Cyproterone acetate". 200 mg daily for cycles of 30 days each.

| | ENDOMETRIO | | | ESTRADIOL p.g./ml | | | ESTRIOL p.g./ml | | |
|---|---|---|---|---|---|---|---|---|---|
| | before treatment | After I cycle | After II cycle | Basal | After I cycle | After II cycle | Basal | After I cycle | After II cycle |
| A. 1979 Age 45 | with some cystic glandular hyperplasic areas | react. decid. stroma | react. decid. stroma | | | | | | |
| N. 41 A. 1980 Age 54 | Cystis glandular hyperplasia | Secretory react. decid. stroma | Secretory react. decid. stroma | 150 | 8.2 | | 13.2 | trace | |

It is evident from those results that in all treated cases a total fall for the estrogen hormones has been achieved. In the Table are also reported the results of the endometrial byopsies, before and after the treatment: they all confirm the high anti-proliferative activity of the Cyproterone acetate on estrogen-progestinic dependent cells.

The obtained results confirm also that, because of its twofold activity which is anti-estrogen on the estrogen extra follicolar biosynthesis and anti-proliferative on the estrogen dependent cells, the Cyproterone acetate can be useful in all cases of post-follicolar iper-estrogen pathology.

What we claim is:

1. The method of treating women having cystic glandular hyperplasia of the endometrium by administering a pharmaceutically-acceptable dosage of cyproterone acetate.

2. The method of claim 1 wherein said dosage is done orally in the range of 200–400 mg daily.

* * * * *

UNITED STATES PATENT AND TRADEMARK OFFICE
CERTIFICATE OF CORRECTION

PATENT NO. : 4,344,942
DATED : August 19, 1982
INVENTOR(S) : MANLIO BLANDAMURA

It is certified that error appears in the above-identified patent and that said Letters Patent is hereby corrected as shown below:

On the title page, add Item /30/ to read:

--[30] Foreign Application Priority Data

July 2, 1980 [IT] Italy ............23191/80

Signed and Sealed this

Fifth Day of October 1982

[SEAL]

Attest:

GERALD J. MOSSINGHOFF

Attesting Officer

Commissioner of Patents and Trademarks